US011864868B2

(12) United States Patent
Akers

(10) Patent No.: US 11,864,868 B2
(45) Date of Patent: Jan. 9, 2024

(54) MODULAR, PORTABLE AND RAPIDLY DEPLOYABLE SYSTEM FOR HEALTH ASSESSMENT

(71) Applicant: Morgan State University, Baltimore, MD (US)

(72) Inventor: Timothy A. Akers, Baltimore, MD (US)

(73) Assignee: Morgan State University, Baltimore, MD (US)

( * ) Notice: Subject to any disclaimer, the term of this patent is extended or adjusted under 35 U.S.C. 154(b) by 620 days.

(21) Appl. No.: 16/711,564

(22) Filed: Dec. 12, 2019

(65) Prior Publication Data

US 2020/0187786 A1    Jun. 18, 2020

Related U.S. Application Data

(60) Provisional application No. 62/778,584, filed on Dec. 12, 2018.

(51) Int. Cl.
*A61B 5/02* (2006.01)
*A61B 5/00* (2006.01)
(Continued)

(52) U.S. Cl.
CPC .............. *A61B 5/02* (2013.01); *A61B 5/339* (2021.01); *A61B 5/4869* (2013.01);
(Continued)

(58) Field of Classification Search
CPC ......... A61B 5/02; A61B 5/339; A61B 5/4869; A61B 5/7435; G16H 10/60; G16H 40/60;
(Continued)

(56) References Cited

U.S. PATENT DOCUMENTS 3,742,932 A    7/1973 Greenspan
5,727,353 A    3/1998 Getz et al.
(Continued)

FOREIGN PATENT DOCUMENTS

WO    WO-2012012527 A2 *   1/2012   .......... C12Q 1/6806

OTHER PUBLICATIONS

A. Sebestyen, G., A. Tirea, and R. Albert. "Monitoring Human Activity through Portable Devices." Carpathian Journal of Electronic and Computer Engineering 5 (2012): 101-6. (Year: 2012).*

*Primary Examiner* — Amber A Misiaszek
(74) *Attorney, Agent, or Firm* — Whiteford, Taylor & Preston, LLP; Gregory M. Stone; Lisa M. Schreihart

(57) ABSTRACT

Disclosed is a modular, portable and rapidly deployable system for health assessment comprising a portable, rapidly deployable structure configured to provide immediate and real-time clinical prevention assessment services, which system allows for rapid assembly and disassembly, immediate deployment to even highly remote locations, and provides basic clinical prevention data and screening for a patient user, along with health education and awareness. In certain configurations, the system comprises modular walls that connect to one another to form the shell of a structure, and a plurality of medical instruments, all of which are configured for self-administration by a medically-untrained user. The user may engage one or more user interface devices that guide the user through the use of each medical instrument and collect the user's clinical data for analysis. Once the desired medical assessment devices have been used and the data collected, the data may be analyzed to provide the user a customized health assessment.

19 Claims, 6 Drawing Sheets

(51) Int. Cl.
*G16H 10/60* (2018.01)
*G16H 50/20* (2018.01)
*G16H 40/63* (2018.01)
*A61B 5/339* (2021.01)
*G16H 40/60* (2018.01)
*G16H 50/80* (2018.01)

(52) U.S. Cl.
CPC ........... *A61B 5/7435* (2013.01); *G16H 10/60* (2018.01); *G16H 40/60* (2018.01); *G16H 40/63* (2018.01); *G16H 50/20* (2018.01); *G16H 50/80* (2018.01)

(58) Field of Classification Search
CPC ........ G16H 40/63; G16H 50/20; G16H 50/80; G16H 10/20; G16H 50/30
See application file for complete search history.

(56) References Cited

U.S. PATENT DOCUMENTS

| | | | |
|---|---|---|---|
| 5,782,045 A | 7/1998 | Paschal | |
| 7,321,862 B2* | 1/2008 | Rosenfeld | G16H 50/20 600/300 |
| 7,411,509 B2* | 8/2008 | Rosenfeld | G16H 50/20 340/286.07 |
| 8,707,630 B1 | 4/2014 | Jhaveri et al. | |
| 2002/0077849 A1* | 6/2002 | Baruch | G16H 70/60 705/2 |
| 2003/0009355 A1* | 1/2003 | Gupta | G06Q 10/10 705/2 |
| 2008/0015423 A1* | 1/2008 | Lam | G16H 10/40 600/300 |
| 2008/0221919 A1 | 9/2008 | Cates | |
| 2009/0259493 A1* | 10/2009 | Venon | G16H 20/10 705/3 |

* cited by examiner

MODULAR, PORTABLE AND RAPIDLY DEPLOYABLE SYSTEM FOR HEALTH ASSESSMENT

CROSS REFERENCE TO RELATED APPLICATIONS

This application is based upon and claims the benefit of U.S. Provisional Application No. 62/778,584 titled "Prevention On Demand Services for Rapid Deployment," filed with the United States Patent & Trademark Office on Dec. 12, 2018, the specification of which is incorporated herein by reference in its entirety.

FIELD OF THE INVENTION

This invention is directed to systems for self-administered health assessments, and more particularly to a portable platform that may quickly be setup in the field to provide remote, self-administered clinical screening services, including data collection, analysis, and information delivery.

BACKGROUND OF THE INVENTION

Research and practice has consistently shown that prevention is the best medicine to stave off disease and illness. Nationally, the U.S. Centers for Disease Control and Prevention (CDC) promotes prevention as the primary method to prevent disease outbreaks, epidemics, and injury, and to increase quality of life. Yet, in areas where healthcare services are scarce, or as in many cases not available at all, prevention is not practiced because of a lack of knowledge about one's own health. In remote areas, such as rural America, urban HubZone areas, military battlefields, or any part of the world, these areas are, in many ways, deserts remote from basic clinical tests and prevention services. Because the "prevention deserts" are removed from the most basic health education, prevention is not often practiced in such areas, simply because citizens and patients, or military personnel, are not informed, taught, or provided basic health screening services, nor do they know their own health status with respect to preventive clinical assessment data. For prevention to work, the most basic clinical assessment data can serve to be the most informative.

Most clinical devices are setup as single points in locations such as doctor's offices, hospitals, and the like. While there may be limited clinical devices deployed in the field, there remains a need in the art for platforms that are highly portable so that they can be readily deployed to the foregoing "prevention deserts," but that also combine multiple clinical devices in a single setting.

SUMMARY OF THE INVENTION

Disclosed herein is a modular, portable and rapidly deployable system for health assessment that avoids one or more disadvantages of the prior art. A system is described herein that provides a portable, rapidly deployable structure configured to provide immediate and real-time clinical prevention assessment services, which system allows for rapid assembly and disassembly, immediate deployment to even highly remote locations, and provides basic clinical prevention data and screening for a patient user, along with health education and awareness.

In an exemplary configuration, and in accordance with certain features of an embodiment, a system is provided comprising modular walls that may be readily connected to one another to form the shell of a structure, and a plurality of medical instruments, all of which are configured for self-administration by a medically-untrained user, thus allowing even remotely located users the ability to obtain a health assessment and customized health-related information. The user may engage one or more user interface devices that guide the user through the use of each medical instrument and collect the user's clinical data for analysis. Once the desired medical assessment devices have been used and the data collected, the data may be analyzed to provide the user a customized health assessment.

In accordance with certain aspects of an embodiment, a modular, portable and rapidly deployable system for health assessment is provided comprising: a plurality of walls joined to one another with removable fasteners, the plurality of walls defining an open interior of a structure; a plurality of medical instruments positioned in the open interior of the structure, wherein each medical instrument enables self-administration of a distinct medical diagnostic exam by a user; and at least one user interface device having computer executable instructions stored thereon configured to present medical instrument usage instructions to the user, receive data from the plurality of medical instruments, and present results of an administration of the medical diagnostic exams to user.

In accordance with further aspects of an embodiment, a system for providing remote health assessment is provided, comprising: a plurality of modular, portable and rapidly deployable units for health assessment, each unit comprising: a plurality of walls joined to one another with removable fasteners, the plurality of walls defining an open interior of a structure; a plurality of medical instruments positioned in the open interior of the structure, wherein each medical instrument enables self-administration of a distinct medical diagnostic exam by a user; and at least one user interface device having computer executable instructions stored thereon configured to present medical instrument usage instructions to the user, receive data from the plurality of medical instruments, and present results of an administration of the medical diagnostic exams to the user; and a remote data processing unit in bidirectional data communication with the plurality of modular, portable and rapidly deployable units for health assessment, wherein the remote data processing unit further comprises computer executable instructions configured to: receive the results of an administration of the medical diagnostic exams from the plurality of modular, portable and rapidly deployable units for health assessment; perform an epidemiological analysis of the results; generate a comparative epidemiological analysis of the results from at least one of the plurality of modular, portable and rapidly deployable units; and transmit results of the comparative epidemiological analysis to the at least one of the plurality of modular, portable and rapidly deployable units.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The numerous advantages of the present invention may be better understood by those skilled in the art by reference to the accompanying drawings in which.

DETAILED DESCRIPTION

Figure 1:
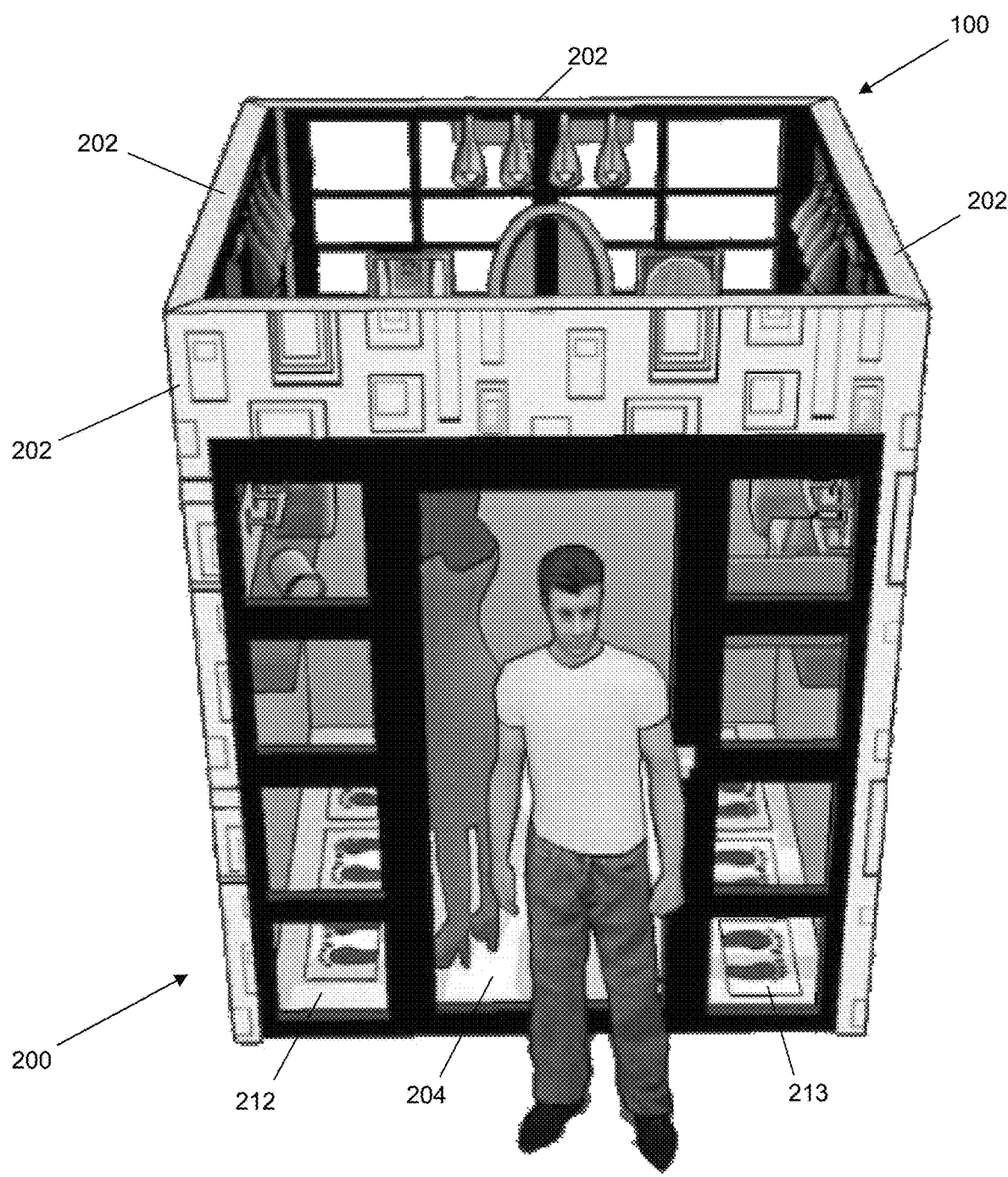
FIG. 1 is a front, perspective view of a modular, portable and rapidly deployable system for health assessment in accordance with certain aspects of an embodiment of the invention.

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Disclosed herein is a portable, rapidly deployable system 100 for health monitoring that enables a user to self-administer a multi-point self-examination through use of a plurality of portable medical instruments positioned within a portable, rapidly deployable structure. As disclosed in greater detail below, system 100 includes a structure 200 comprising multiple walls 202, one of which includes a doorway opening 204 allowing a user to enter and exit an assembled structure 200. Mounted on the interior of at least some of walls 202 are portable medical instruments 210, each of which is configured for operation by a user without requiring that such user have specialized medical training. One or more user interface devices 220 are likewise positioned inside of structure 200 and are operable preferably to provide a user instructions on use of each medical instrument 210 inside of structure 200, to collect medical data generated by each medical instrument 210 as the user engages each medical instrument 210, and to provide feedback to the user, such as an assessment of their medical condition as determined through analysis of the clinical data generated by medical instruments 210. Such a system offers a comprehensive, self-serve, multi-point self-examination to empower users through education of their current health condition to, in turn, offer a better quality of life. The system offers a portable and rapidly deployable system for health education, health literacy, health screening, and health promotion that helps to identify early warning signs of risky health threats and health disparities, and that helps to manage better overall health outcomes. The system also provides rapid biomedical and behavioral metrics on an individualized basis and in real-time.

Figure 3:
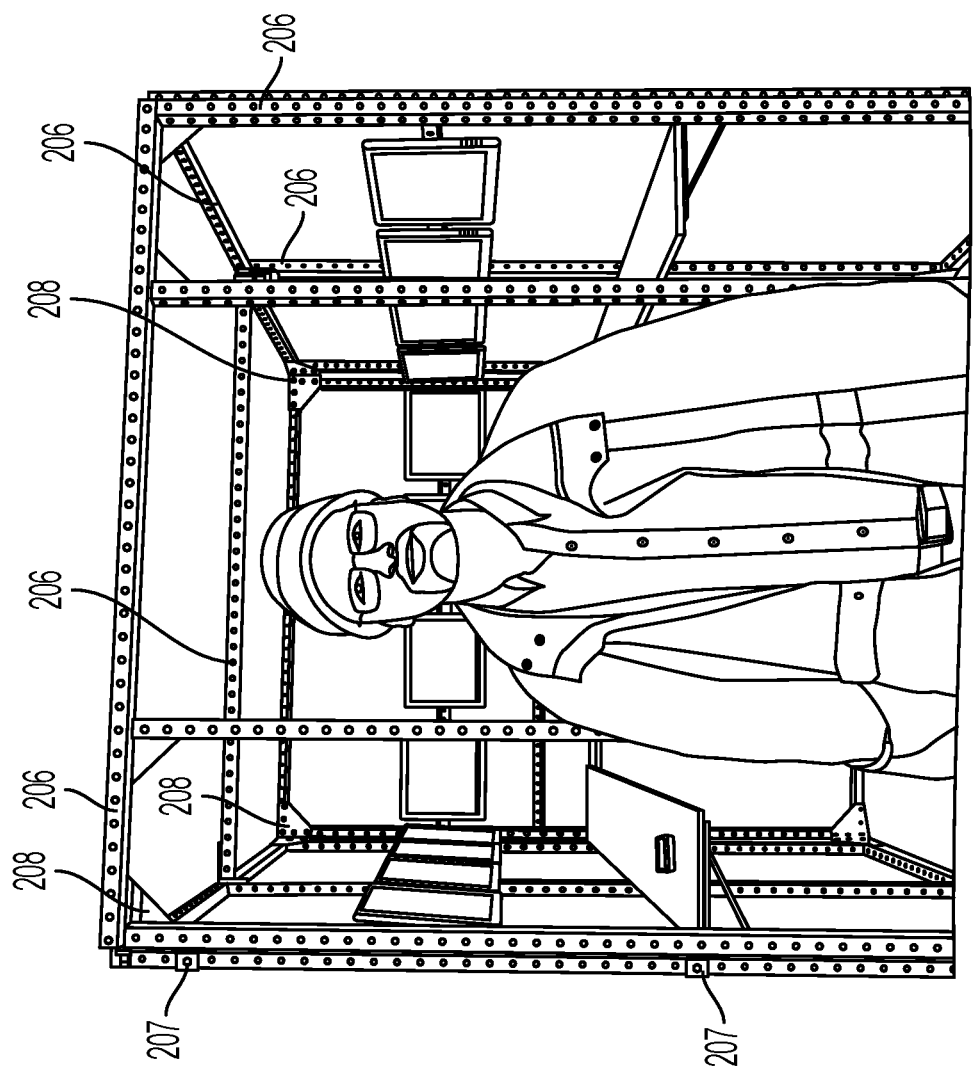
FIG. 3 is a front perspective view of interior support members forming a portion of the system of FIG. 1.

As shown in FIG. 3, structure 200 is formed by support members 206 that create a skeletal frame for structure 200. Support members 206 comprise elongate, metal studs having openings extending there through that may receive bolts or similar removable connecting members to allow adjacent support members 206 to be quickly connected to one another. L-brackets 207 may be used to attach adjacent, vertically-oriented support members 206. Likewise, corner brackets 208 may be affixed to intersecting support members 206 at corners of structure 200, and particularly preferably spanning at least the top and bottom interior corners of structure 200 to provide fixed, rigid support to those corners. Corner brackets 208 are similarly affixed to support members via bolts or similarly configured removable connecting members for rapid assembly and disassembly of structure 200. Further, in addition to support members 206 forming the outline of structure 200, support members 206 may also be positioned along wall sections of structure 200, such as at a middle of one of the walls of structure 200, to offer added rigidity to structure 200 while still enabling rapid setup and disassembly. In certain particularly preferred configurations, structure defines an interior space of 35-36 ft$^2$.

Figure 2:
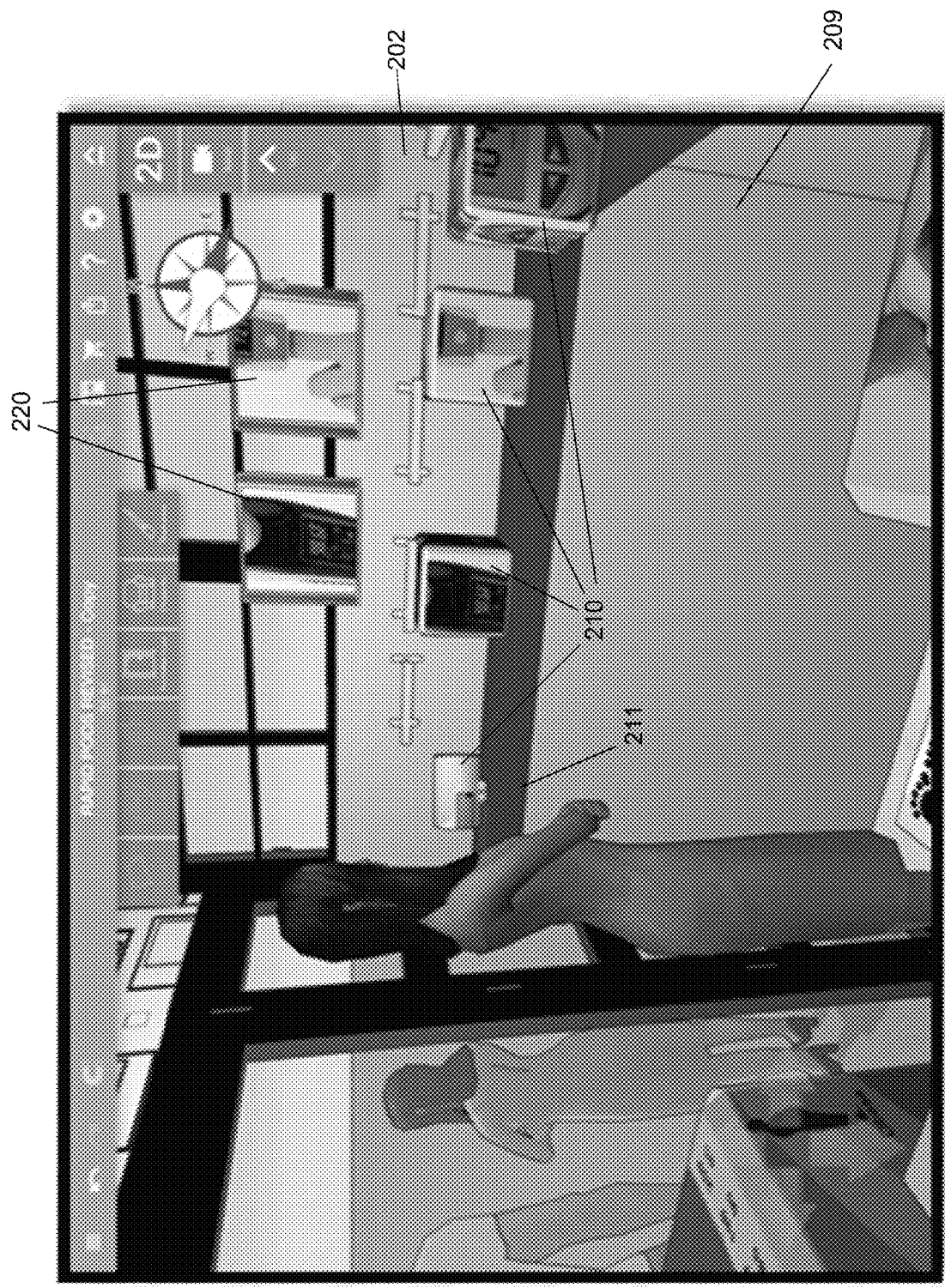
FIG. 2 is a perspective view of a portion of the interior of the system of FIG. 1.
Figure 4:
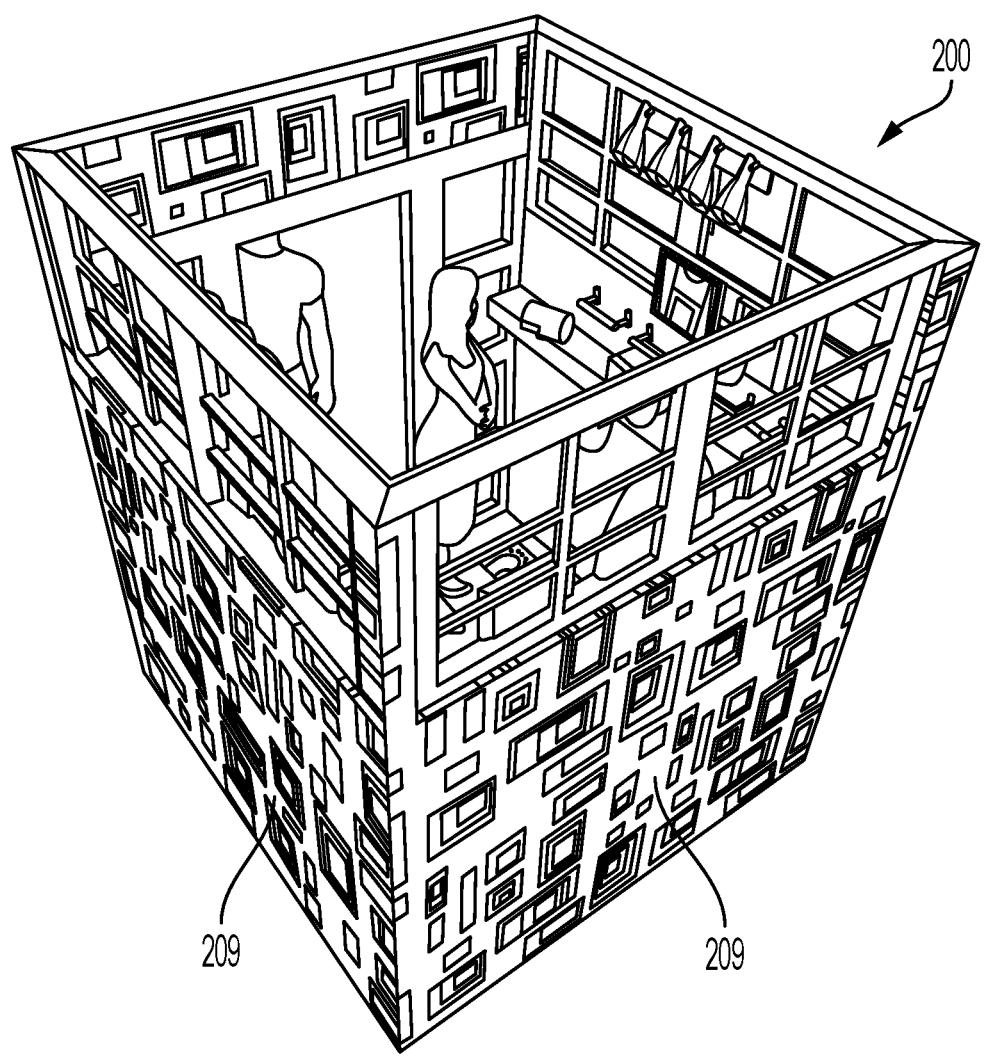
FIG. 4 is a rear, perspective view of the system of FIG. 1.

With reference to FIGS. 2 and 4, wall panels 209 are provided both on the interior and exterior of structure 200, and are configured for quick attachment to and removal from support members 206. By way of non-limiting example, wall panels 209 may attach to support member 206 by way of hooks engaging the openings in support members 206, threaded members extending through wall panels 209 and into the openings in support members 206, or such other attachment mechanisms as will be realized by those of ordinary skill in the art, and that will allow for the temporary attachment and ready removal of wall panels from support members 206 to maintain an easily deployable and disassembled structure.

Preferably, shelf units 211 are provided on the interior of structure 200 and extending horizontally around the interior wall panels 209. Shelf units 211 are preferably similarly joined to support members 206 with threaded connectors that may extend through wall panels 209 and into the openings in support members 206, again allowing their quick connection and disassembly from structure 200. Shelf units 211 are preferably positioned to mount medical instruments 210 at a height that allows users to access such medical instruments 210, preferably without having to bend or squat, while likewise being readily accessible to a person in a wheelchair without requiring that they stand or otherwise exit from the wheelchair. Further, one or more wall-mounted, fold-out seating units may be affixed to wall panels 209 below shelf units 211 to optionally allow a user to sit during self-administration of a test using one of medical instruments 210. Optionally, multiple wall-mounted, fold-out seating units may be provided around the interior of structure 200 to allow a user to be seated at a plurality of, and optionally all of, the locations intended for administration of a test via a medical instrument 210.

User interface devices 220, which may comprise (by way of non-limiting example) tablets preferably each equipped with a touch screen display, a speaker, and a microphone, are provided inside of structure 200, and may be mounted to the interior wall panels 209 above each medical instrument 210. User interface devices 220 are configured to provide instructions to the user on how to use each medical instrument 210, to receive data generated from each medical instrument after a user has engaged such medical instrument 210 (either through the user manually inputting that data on a data entry screen presented by user interface device 220, or through direct wired or wireless communication with the respective medical instrument 210), to transmit such data to a local processing hub in structure 200 or a remote processing hub for processing and storage of the user's medical data collected from medical instruments 210, and to communicate results and other health related information back to the user.

Optionally, instead of multiple user interface devices 220, a single user interface device 220 may be provided that may be moved from one medical instrument 210 to the next as the user progresses through each diagnostic step offered by system 100, with the user interface device 220 being configured to sequentially step through each test administered by each medical instrument 210. For example, a table mount may be movably attached to a rail or bar that is affixed to shelf units 211, such that a user may slide the user interface device 220 along such rail or bar as they move from one medical instrument 210 to the next.

In each case, user interface devices 220 may, in certain configurations, have a touch screen that displays a person providing pre-recording instructions for use of each medical instrument 210, along with selections or data entry fields that a user engages to enter their relevant data. While the system is preferably configured to enable automatic data collection from medical instruments 210, prompting the user to enter the data generated by each medical instrument may offer an added benefit of empowering the user by requiring that they engage and participate in their own health screening, health education, health promotion, and health literacy. Optionally, user interface devices 220 also allow the user to engage in two-way communication with a remote clinician, such as a nurse practitioner, who is in remote data communication (whether via text, video chat, or otherwise) with system 100. Once the user selects such clinical interaction, the remote clinician preferably appears on the screen to interact with the user.

Optionally, a floor or partial floor 212 may be provided in structure 200. In such configurations, foot position pads 213 may be provided on floor 212 that direct the user to the proper position to engage each respective medical instrument 210.

As the foregoing components of structure 200 are all configured for quick connection and thus easy deployment and dismantling, the entire structure is highly portable and can readily be moved and deployed to a needed location. For instance, each of support members 206, wall panels 209, and shelf units 211 may be shipped flat, thus enabling easy packaging and transport of the structural elements of structure 200. In certain configuration, fully assembled walls 202 (including that wall's support members 206 and wall panels 209) may be pre-assembled and then stood up and connected to other walls 202 to form structure 200, and may likewise be prewired with all communication and power cabling for medical instruments 210 and user interface devices 220. In order to further enhance the portability of system 100, wheels (not shown) may be attached to the bottom of support members 206 to allow structure 200 to be rolled to a desired position once placed and assembled at a given location. Likewise, the exterior of structure 200 may be provided a towing bar allowing connection to a vehicle for moving structure 200 longer distances, may be placed on a trailer for moving structure 200 still longer distances, and may be provided with structurally reinforced corners with connecting hooks for lift straps (all of standard configuration) to allow for helicopter lift and transport for even longer distances while maintaining the structural rigidity of structure 200. Even further, structure 200 may be sized for fitment within a standard cargo/container shipping unit.

Figure 5:
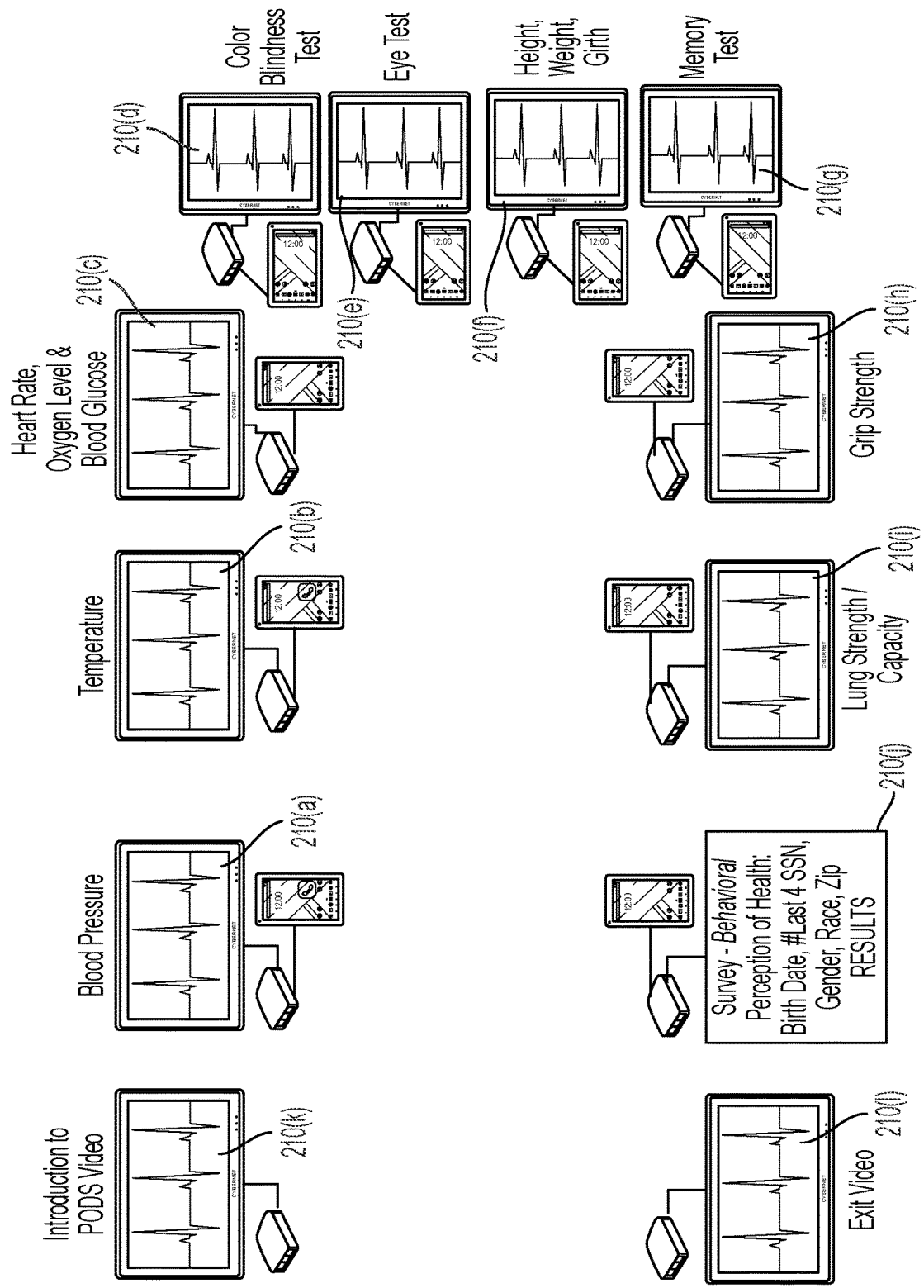
FIG. 5 is a schematic view of medical instruments for use in the system of FIG. 1.

Next, FIG. 5 is a schematic view of exemplary medical instruments 210 that may be employed in system 100, each of which is preferably portable and readily used to administer the respective test by a non-medical-professional user. Such medical instruments are preferably commercially readily available devices of configurations that are generally known to those skilled in the art, such that the operational details of those medical instruments are not further discussed here. However, such medical instruments 210 employed by system 100 will preferably include some collection of the following: a blood pressure test 210(a); a temperature test 210(b); a heart rate, blood oxygen level, and optionally blood glucose level test 210(c); a color blindness test 210(d); an eye/vision test 210(e); a height, weight, and girth/BMI index test 210(f); a memory test 210(g); a grip strength test 210(h); a lung strength/capacity test 210(i); and a survey and results interface 210(j) configured to solicit behavioral data relating to the user's health and the user's biographical details, and to communicate the results of the user's self-assessment. Optionally, additional stations may be provided to display an introductory video 210(k) before the user begins the self-assessment, and an exit video 210(l) after the user has completed the self-assessment. Further, those of ordinary skill in the art will recognize that other portable medical diagnostic devices may be included beyond those set forth above without departing from the spirit and scope of the invention.

Figure 6:
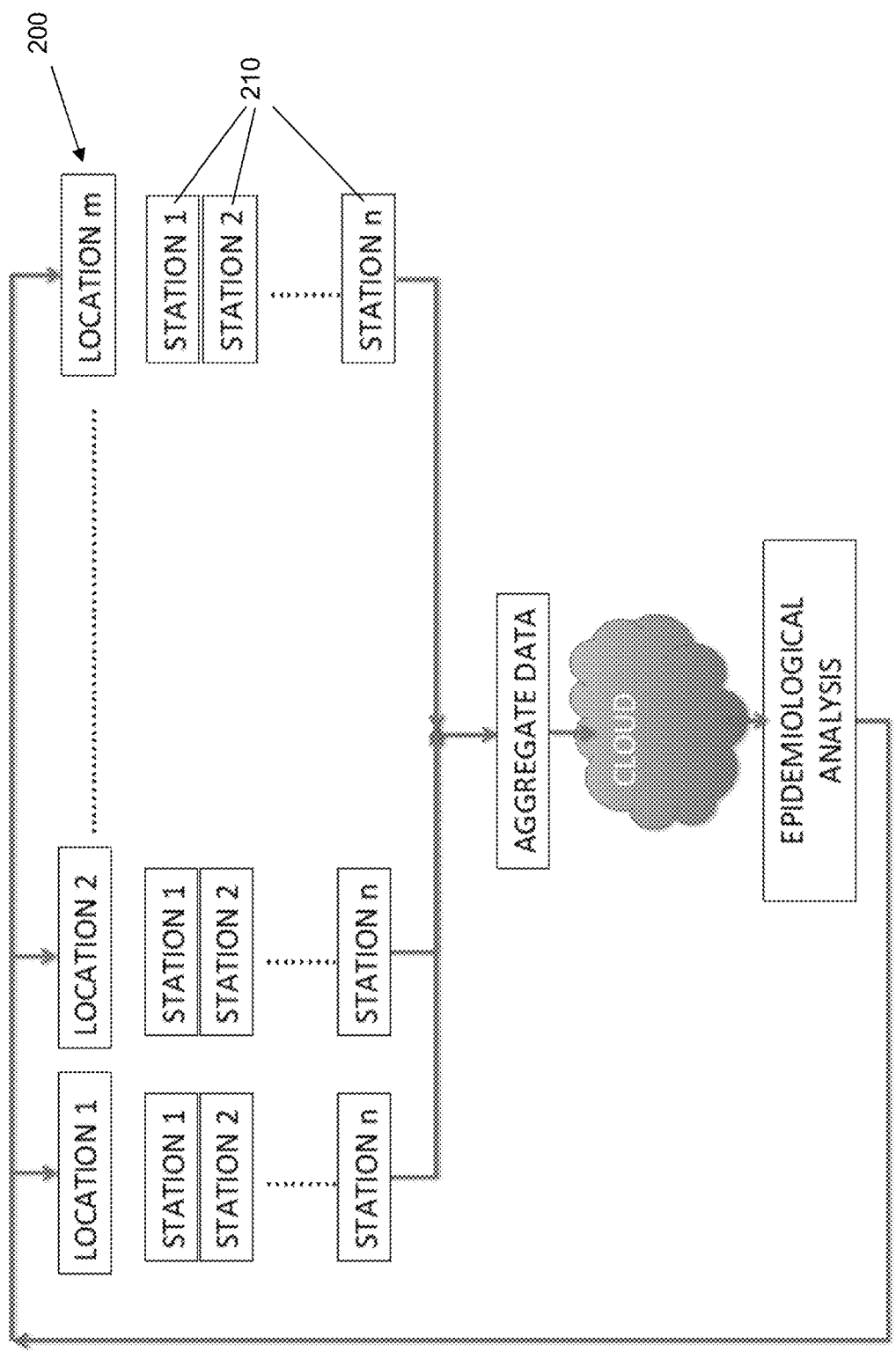
FIG. 6 is a schematic view of a data processing system for processing data from multiple modular, portable and rapidly deployable systems for health assessment in accordance with certain aspects of an embodiment of the invention.

Preferably, all of the clinical data collected by medical instruments 210(a)-210(j) is aggregated to create a record for that individual user. For example, the data collected by medical instruments 210(a)-210(j) may communicate with a local processing unit at structure 200 to create a patient record for that individual user. Once that patient record has been created, it may then optionally be communicated (for example via a wireless communication device or via connection to a wide area network such as the Internet) to a remote data processor and/or repository which may be accessible, for example, in a cloud computing environment. As shown in the schematic view of FIG. 6, multiple structures 200 may collect data from their respective medical instruments 210, and may separately and independently upload that data for epidemiological analysis at a remote data processor. That remote data processor and/or repository may track each visit by each user for purposes of incident tracking and trend analysis. Optionally, that remote data processor may, with authorization of the user, carry out real-time epidemiologic comparative analysis of the user's data, with the results of that analysis and the user's individualized results being transmitted back to the user in real-time at the location of the user's respective structure 200.

Upon completion of the analysis, and as mentioned briefly above, the user may receive the results of the analysis at medical instrument 210(*j*). In certain exemplary configurations, at that stage the user may have the options to (i) print their results for personal use and viewing, (ii) send their results to their own clinician for basic analysis and clinical recommendations for a subsequent visit to their clinician, (iii) send the result to a live clinical network partner, such as a nurse practitioner or other specialist that is in data communication with system 100, (iv) send results to their telephone via text message or email, and (v) send their results to a software application that may show the user's number of visits, health trends, and other data as may occur to those skilled in the art.

Additionally, in certain configurations, system 100 may include a data card reader and writer configured to (i) write user biographical/identification information and their related results to a data card that the user may take with them after use of system 100, and (ii) read such data from the card for subsequent visits to track the user's medical history and changes to their medical health status. Preferably, such data card reader may also be configured to automatically read data from the user's medical insurance card, driver's license, and such other data-carrying cards that may be relevant to the user's identification and medical history.

Preferably, in order to maintain patient privacy, access within each location will require that only authorized personnel are able to review data and results of any corresponding analysis.

The foregoing system offers a portable, readily deployable health assessment tool that does not require medical staff to be present to use, that may be engaged by individuals at any time, and that allow for results of a user's health assessment to be uploaded onto a personal medical card, or delivered electronically to a medical practitioner through a secured cloud server.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A modular, portable and rapidly deployable system for health assessment, comprising:
   a plurality of walls joined to one another with removable fasteners, said plurality of walls defining an open interior of a structure;
   a plurality of medical instruments positioned in said open interior of said structure, wherein each said medical instrument enables self-administration of a distinct medical diagnostic exam by a user;
   a slidably affixed user interface device having computer executable instructions stored thereon configured to:
      detect one of said plurality of medical instruments as said slidably affixed user interface device is positioned in proximity to said one of said plurality of medical instruments;
      upon detection of said one of said plurality of medical instruments, communicatively connect said slidably affixed user interface device to said one of said plurality of medical instruments;
      present medical instrument usage instructions of said one of said plurality of medical instruments to said user for administering a corresponding distinct medical diagnostic exam;
      receive data from said one of said plurality of medical instruments;
      present user-individualized results of an administration of said corresponding distinct medical diagnostic exam to said user in real-time at said structure; and
      communicatively disconnect said slidably affixed user interface device from said one of said plurality of medical instruments upon user acknowledgement of said user-individualized results; and
   a remote data processor in data communication with said plurality of medical instruments, wherein said remote data processor further comprises computer executable instructions stored thereon configured to:
      aggregate said data for said user from said plurality of medical instruments;
      perform a real-time epidemiological analysis of said aggregated data from said plurality of medical instruments;
      transmit results of said real-time epidemiological analysis back to said slidably affixed user interface device at completion of said real-time epidemiological analysis; and
      transmit said user-individualized results with said results of said real-time epidemiological analysis to a remote clinician in response to an authorization by said user at said slidably affixed user interface device.

2. The system of claim 1, further comprising a plurality of additional user interface devices, wherein each said additional user interface device is configured to receive and process said data from a single one of said medical instruments.

3. The system of claim 1, wherein said slidably affixed user interface device is movably mounted on a rail affixed along said open interior of said structure and is slidable to positions adjacent to each of said medical instruments along the rail.

4. The system of claim 1, said plurality of walls of said structure further comprising an entry wall including a doorway opening, and a plurality of non-entry walls, wherein said medical instruments further comprise at least one medical instrument positioned along an interior side of each non-entry wall of said structure.

5. The system of claim 4, wherein said medical instruments are selected from the group consisting of a blood pressure test, a temperature test, a heart rate test, a blood oxygen level test, a blood glucose level test, a color blindness test, a vision test, a height measurement, a weight measurement, a BMI measurement, a memory test, a grip strength test, and a lung capacity test.

6. The system of claim 1, further comprising a card reader and writer.

7. The system of claim 6, wherein said card reader and writer is configured to write said user-individualized results of said administration of said medical diagnostic exams to said user to a data card.

8. The system of claim 7, wherein said card reader and writer is further configured to read at least one of a user's driver's license and health insurance card.

9. The system of claim 1, further comprising shelf units removably attached to an interior of said walls of said structure.

10. The system of claim 9, wherein said medical instruments further comprise at least one medical instrument positioned on each said shelf unit, wherein each said shelf unit is joined to each of other said shelf units by a rail affixed to said shelf units.

11. A system for providing remote health assessment, comprising:
a plurality of modular, portable and rapidly deployable units for health assessment, each said unit comprising:
a plurality of walls joined to one another with removable fasteners, said plurality of walls defining an open interior of a structure;
a plurality of medical instruments positioned in said open interior of said structure, wherein each said medical instrument enables self-administration of a distinct medical diagnostic exam by a user; and
a slidably affixed user interface device having computer executable instructions stored thereon configured to:
detect one of said plurality of medical instruments as said slidably affixed user interface device is positioned in proximity to said one of said plurality of medical instruments;
upon detection of said one of said plurality of medical instruments, communicatively connect said slidably affixed user interface device to said one of said plurality of medical instruments;
present medical instrument usage instructions of said one of said plurality of medical instruments to said user for administering a corresponding distinct medical diagnostic exam;
receive data from said one of said plurality of medical instruments;
present user-individualized results of an administration of said corresponding distinct medical diagnostic exam to said user in real-time at said structure; and
communicatively disconnect said slidably affixed user interface device from said one of said plurality of medical instruments upon user acknowledgement of said user-individualized results; and
a remote data processing unit in bidirectional data communication with said plurality of modular, portable and rapidly deployable units for health assessment, wherein said remote data processing unit further comprises computer executable instructions configured to:
receive said user-individualized results of said administration of said medical diagnostic exams from said plurality of modular, portable and rapidly deployable units for health assessment;
perform a real-time epidemiological analysis of said user-individualized results;
generate a comparative epidemiological analysis of said user-individualized results from at least one of said plurality of modular, portable and rapidly deployable units;
transmit results of said comparative epidemiological analysis to said at least one of said plurality of modular, portable and rapidly deployable units; and
transmit said user-individualized results to a remote clinician in response to an authorization by said user at said slidably affixed user interface device.

12. The system of claim 11, wherein each said unit further comprises a plurality of additional user interface devices, wherein each said additional user interface device is configured to receive and process said data from a single one of said medical instruments.

13. The system of claim 11, wherein each said slidably affixed user interface device is movably mounted on a rail affixed along said open interior of said structure and is slidable to positions adjacent to each of said medical instruments along the rail.

14. The system of claim 11, wherein said plurality of walls of each said structure further comprises an entry wall including a doorway opening, and a plurality of non-entry walls, wherein said medical instruments further comprise at least one medical instrument positioned along an interior side of each non-entry wall of said structure.

15. The system of claim 14, wherein said medical instruments are selected from the group consisting of a blood pressure test, a temperature test, a heart rate test, a blood oxygen level test, a blood glucose level test, a color blindness test, a vision test, a height measurement, a weight measurement, a BMI measurement, a memory test, a grip strength test, and a lung capacity test.

16. The system of claim 11, wherein each said unit further comprises a card reader and writer.

17. The system of claim 16, wherein each said card reader and writer is configured to write said user-individualized results of said administration of said medical diagnostic exams to said user to a data card.

18. The system of claim 17, wherein each said card reader and writer is further configured to read at least one of a user's driver's license and health insurance card.

19. The system of claim 11, wherein each said unit further comprises shelf units removably attached to an interior of said walls of said structure, and wherein said medical instruments further comprise at least one medical instrument positioned on each said shelf unit, wherein each said shelf unit is joined to each of other said shelf units by a rail affixed to said shelf units.

* * * * *